United States Patent
Hoffmann et al.

(10) Patent No.: US 6,805,119 B2
(45) Date of Patent: Oct. 19, 2004

(54) DEVICE FOR CONTROLLING A BREATHING GAS FLOW

(75) Inventors: Karsten Hoffmann, Kasseed/Griebel (DE); Olaf Wohlenberg, Heidekamp (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 0 days.

(21) Appl. No.: 10/349,222

(22) Filed: Jan. 22, 2003

(65) Prior Publication Data
US 2003/0200968 A1 Oct. 30, 2003

(30) Foreign Application Priority Data
Apr. 30, 2002 (DE) .......................................... 102 19 286

(51) Int. Cl.$^7$ ...................... A61M 16/00; F23D 11/00; F23D 14/00
(52) U.S. Cl. ............................ 128/203.26; 128/203.17; 128/203.27
(58) Field of Search ....................... 128/203.26, 203.27, 128/205.28, 203.16, 203.17, 204.14

(56) References Cited

U.S. PATENT DOCUMENTS

| 4,982,207 A | * | 1/1991 | Tunmore et al. ............. 346/138 |
| 5,259,370 A | * | 11/1993 | Howe ..................... 128/200.14 |
| 5,978,548 A | * | 11/1999 | Holmstrand et al. ........ 392/397 |
| 6,234,167 B1 | * | 5/2001 | Cox et al. ............... 128/200.14 |
| 6,367,472 B1 | * | 4/2002 | Koch ..................... 128/203.12 |

FOREIGN PATENT DOCUMENTS

DE      3629353 C1 * 1/1988 .......... A61M/16/10

* cited by examiner

*Primary Examiner*—Glenn K. Dawson
*Assistant Examiner*—Michael G. Mendoza
(74) *Attorney, Agent, or Firm*—McGlew and Tuttle, P.C.

(57) ABSTRACT

A device for controlling the breathing gas flow is provided including a breathing gas block (2), a cover (4) and a valve plate (3) as well as a heating device. Condensation effects are prevented from occurring with the supply of the smallest possible amount of energy by provision of a heating foil (16) as a heating element.

22 Claims, 4 Drawing Sheets

DEVICE FOR CONTROLLING A BREATHING GAS FLOW

FIELD OF THE INVENTION

The present invention pertains to a device for controlling a breathing gas flow, with the device containing a breathing gas block with a cover enclosing a breathing gas space, as well as a heating device for the breathing gas space.

BACKGROUND OF THE MENTION

A device for controlling the breathing gas flow, with a breathing gas block, a cover and a valve plate accommodated in a sandwich-like manner between the breathing gas block and the cover, has become known from DE 36 29 353 C1. The breathing gas, with which a patient is respirated, flows through the breathing gas block in various channels. The channels are open toward the valve plate and are able to be closed or released by means of closing elements, which are arranged at the valve plate. The closing elements are actuated pneumatically from the cover by a corresponding control pressure being admitted to individual control pressure spaces, which are associated with the closing elements.

The breathing gas circulating in a breathing circuit is normally enriched with water vapor up to the saturation limit during the return of the expired breathing gas, as a result of which condensation of water vapor may take place in the breathing gas block, but also on the side of the valve plate facing the breathing gas block. To prevent such condensation effects, the material of the breathing gas block is designed in the prior-art device as an electrically conductive heating device and is uniformly heated in all areas by a current flowing through. It was found that the condensate formation within the breathing gas block is subject to very great variations and it is only insufficiently possible to respond to it with a uniform heating of the breathing gas block. To also prevent condensation in the area of problematic condensate traps, the breathing gas block would have to be heated at about 40° C. However, such surface temperatures are not acceptable for functional reasons. In addition, a not inconsiderable heat output is also necessary to maintain the entire breathing gas block at this temperature, especially because part of the heat is again removed by heat conduction by adjacent components, e.g., a respiration pump.

SUMMARY OF THE INVENTION

The basic object of the present invention is to improve a device of this type such that condensation effects are prevented from occurring with a supply of the smallest possible amount of energy.

According to the invention, a device for controlling the breathing gas flow is provided with a breathing gas block with a cover, which enclose a breathing gas space. A heating device for the breathing gas space is provided. A heating foil is provided as the heating element.

The advantage of the present invention is essentially that condensation can be effectively prevented from occurring by the heating device being designed as one or more heating foils, which are fastened within the breathing gas space enclosed by the breathing gas block and the cover at the points at which the heat output is needed. The heating foil may be applied flatly at the points that are especially susceptible to the condensation of water vapor, as a result of which the heat output supplied can be metered better. It is also possible to supply different heat outputs via the heating foils, so that problem zones can be heated more intensely than other areas, in which only a small amount of condensate is formed, without excessively high surface temperatures developing on the outside of the breathing gas block and the cover.

The heating foils may also be arranged such that they can line breathing gas-carrying channels.

Heating foils preferably consist of a flexible carrier material, in which heating wires are embedded in a meandering manner. However, it is also possible to design the heating foil as a flat resistor element in order to achieve a more uniform distribution of the heat or to apply heating elements in the form of a coating, corresponding to a printed circuit board, to the carrier material.

It is especially advantageous to integrate at least one temperature sensor in the heating foil in order to determine the heating temperature directly at the site of the heating foil. It is especially expedient to arrange more than one temperature sensor on the heating foil to make it possible to measure temperature mean values, on the one hand, and, on the other hand, to be also able to continue to operate the heating foil when a temperature sensor fails. It is also possible to use one of the temperature sensors for the temperature regulation and the other temperature sensor as a pure temperature monitoring sensor.

It is especially advantageous to arrange the heating foil directly at a valve plate, which is located between the breathing gas block and the cover. Since the valve plate partially covers breathing gas channels of the breathing gas block, problematic breathing gas channels can be effectively heated via the valve plate. If the valve plate consists of metal, there is good thermal conduction within the valve plate, so that a single heating foil is normally sufficient to heat the valve plate.

It is especially advantageous to insert the heating foil into an opening located at the valve plate and to seal it with a sealing compound. By sealing in the heating foil, damage that could occur, e.g., during sterilization or the processing is prevented from occurring. The arrangement of the heating foil in the area of the valve plate is especially advantageous also because only the valve plate must be replaced in case of a defect of the heating foil.

It is advantageous to connect the heating point electrically to a control unit via detachable contact means. The control unit processes the measured temperature values and regulates the current flowing through the heating foil corresponding to a preset set point for the temperature. The contacting is preferably performed by means of gold-plated, spring-loaded contact pins, which are electrically connected to corresponding contact surfaces on the heating foil. The contact surfaces have replaceable contact screws, so that contacts can also be replaced individually, without the entire valve plate together with the heating foil having to be replaced.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
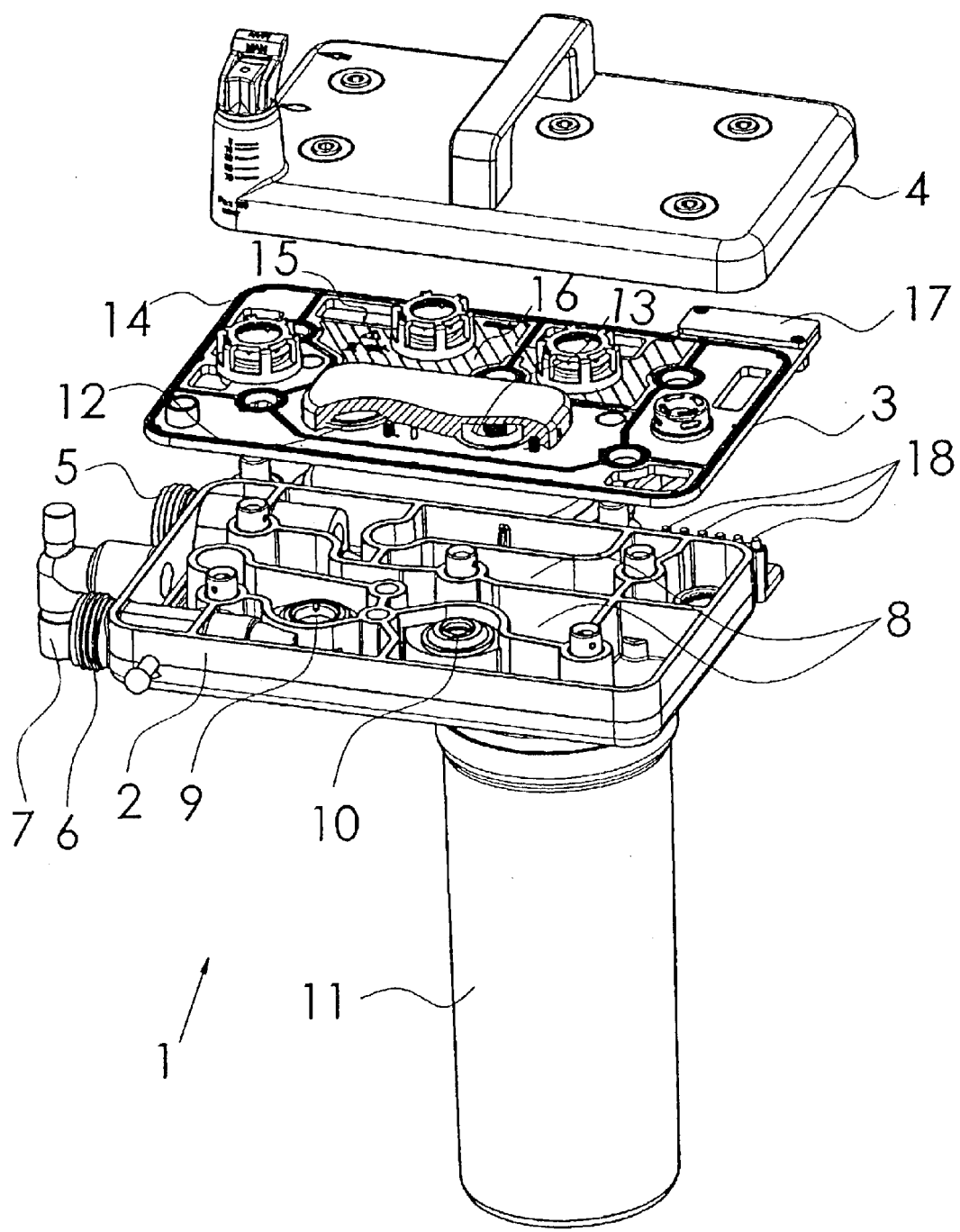
FIG. 1 is an exploded perspective view of a respirator for controlling the breathing gas flow.

Referring to the drawings in particular, FIG. 1 shows a perspective view of a respirator 1, which, having a layered structure, comprises a breathing gas block 2, a valve plate 3 and a cover 4. The breathing gas block 2 is provided with breathing gas connections 5, 6, 7, via which a patient, not shown in FIG. 1, is supplied with breathing gas. Breathing gas channels 8 with corresponding valve spaces 9, 10 are located within the breathing gas block 2 to control the direction of the breathing gas flow within the breathing gas block 2 in the cycle of breathing in and breathing out. A carbon dioxide absorber 11 arranged under the breathing gas block 2 removes carbon dioxide from the breathing gas. The valve plate 3 lying on the breathing gas block 2 has closing elements 12, 13, to which a control pressure can be admitted via control pressure lines not shown specifically in FIG. 1 and which either interrupt or release the breathing gas flow through the valve spaces 9, 10. Sealing cords 14 extending above the valve plate 3 divide the valve plate 3 into individual breathing gas spaces. Corresponding sealing cords, which are not shown in FIG. 1, are also located on the underside of the valve plate 3 in order to separate breathing gas channels 8 and valve spaces 9, 10 from each other. A heating foil 16, which is sealed with a silicone compound, which is not shown in detail in FIG. 1, is inserted into an opening 15 on the top side of the valve plate 3. The electric contacting of the heating foil is performed via a contact element 17 led to the outside at the valve plate 3 and via spring-loaded contact pins 18 at the breathing gas block 2.

Figure 2:
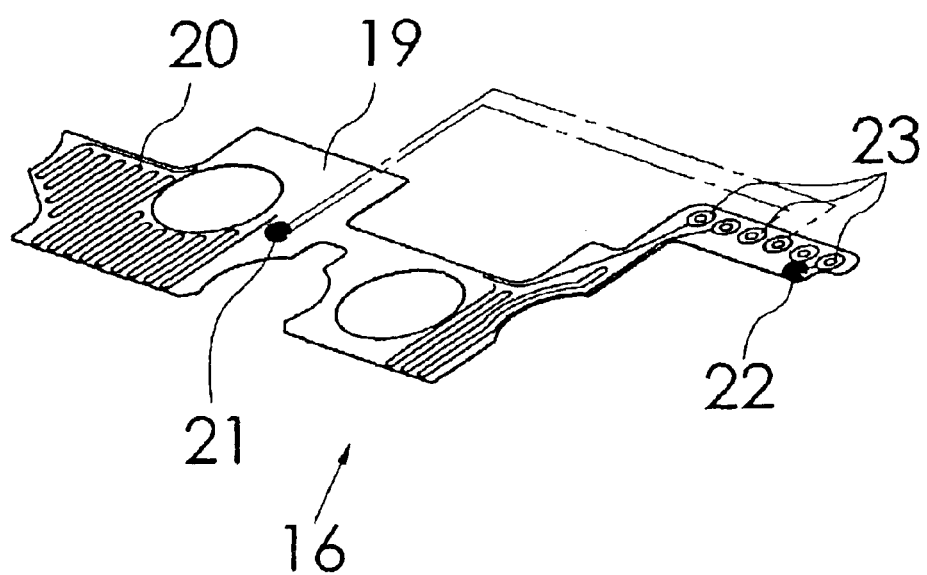
FIG. 2 is a perspective view of a heating foil according to the present invention corresponding to FIG. 1.

FIG. 2 shows a perspective view of the heating foil 16 according to FIG. 1. The heating foil 16 consists of a carrier material 19, in which heating wires 20 are embedded in a meandering manner. The carrier material 19 is used, furthermore, to accommodate two temperature sensors 21, 22. The heating wires 20 and the temperature sensors 21, 22 are connected to individual contact surfaces 23 at the heating foil 16.

Figure 3:
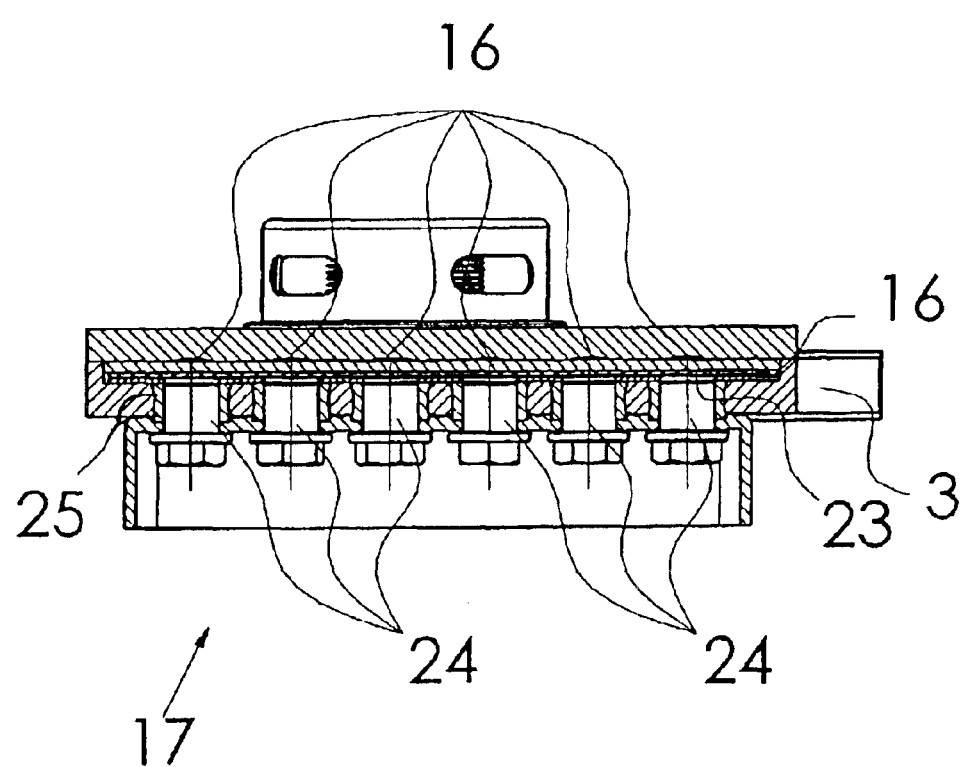
FIG. 3 is a cross-sectional detail view of a valve plate with inserted heating foil in the area of the contacting.
Figure 4:
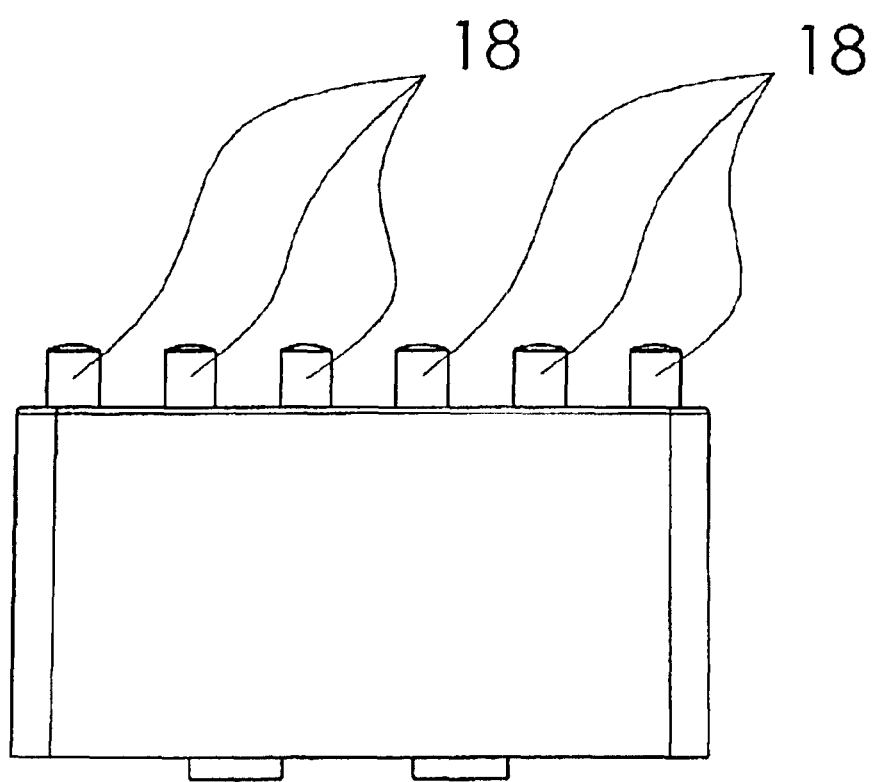
FIG. 4 is a view showing spring-loaded contact pins for contacting the contacts according to FIG. 3.

FIG. 3 shows a detail of the valve plate 3 in the area of the contact element 17 of the heating foil 16. The contact surfaces 23 are electrically connected to replaceable contact screws 24, which are inserted into insulating bushes 25 at the valve place 3. Spring-loaded contact pins 18 under the contact element 17, corresponding to FIG. 4, establish the connection to a control and regulating unit, not shown more specifically in the figures, which is used to set a predetermined temperature of the heating foil 16. The temperature sensors 21, 22 determine the actual value of the temperature independently from one another.

While a specific embodiment of the invention has been shown and described in detail to illustrate the application of the principles of the invention, it will be understood that the invention may be embodied otherwise without departing from such principles.

What is claimed is:

1. A device for controlling the breathing gas flow, the device comprising:
   a breathing gas block;
   a cover, said block and said cover cooperating to enclose a breathing gas space; and
   a heating device for heating the breathing gas space, the heating device including a heating foil provided as a heating element;
   a valve plate arranged at a location between said breathing gas block and said cover, said heating foil being arranged at said valve plate.

2. A device in accordance with claim 1, further comprising a temperature sensor integrated within the heating foil for determining the heating temperature.

3. A device in accordance with claim 1, wherein:
   said heating foil is fastened within said breathing space.

4. A device in accordance with claim 1, wherein said heating foil is inserted into an opening located at said valve plate and said heating foil is sealed with a sealing material.

5. A device in accordance with claim 1, further comprising a detachable contact wherein said heating foil is electrically connected to said detachable contact.

6. A device in accordance with claim 5, wherein said contact comprises spring-loaded contact pins and corresponding contact screws, wherein said contact pins are in contact with said contact screws.

7. A device in accordance with claim 6, wherein said contact pins or said contact screws are designed such that they are individually replaceable.

8. A breathing gas low control system comprising:
   a breathing gas block with breathing gas connections;
   a cover, said block and said cover cooperating to enclose breathing gas channels;
   a valve part arranged at a location between said breathing gas block and said cover; and
   a heating device for heating one or more of breathing gas channels, the heating device including a heating foil arranged on said valve part.

9. A breathing gas flow control system in accordance with claim 8, further comprising a temperature sensor integrated within the heating foil for determining the heating temperature.

10. A breathing gas flow control system in accordance with claim 8, wherein said heating foil is inserted into an opening located at said valve part and said heating foil is sealed with a sealing material.

11. A breathing gas flow control system in accordance with claim 8, further comprising a detachable contact wherein said heating foil is electrically connected to said detachable contact.

12. A breathing gas flow control system in accordance with claim 11, wherein said contact comprises spring-loaded contact pins and corresponding contact screws, wherein said contact pins are in contact with said contact screws.

13. A breathing gas flow control system in accordance with claim 12, wherein said contact pins or said contact screws are individually removable and replaceable.

14. A method of providing a breathing gas flow control device, the method comprising:
   forming a breathing gas block with breathing gas spaces and breathing gas connections;
   connecting a valve plate to the block;
   positioning a heating foil as a heating element adjacent to one or more of the breathing gas spaces; and placing a cover over the block, the block and the cover cooperating to enclose the spaces as breathing gas conduits with the heating foil disposed adjacent to one or more of the conduits;

positioning the heating foil on the valve plate.

15. A method in accordance with claim 14, further comprising integrating a temperature sensor within the heating foil and determining a heating temperature during use.

16. A method in accordance with claim 14, wherein said heating foil is inserted into an opening located at said valve plate and said heating foil is sealed with a sealing material.

17. A method in accordance with claim 14, further comprising providing a detachable contact in electrical connection with the heating foil, the contact comprising spring-loaded contact pins and corresponding contact screws, wherein the contact pins are in contact with the contact screws.

18. A method in accordance with claim 17, further comprising individually removing and replacing the contact pins or the contact screws.

19. A method of providing a breathing gas flow control device, the method comprising:

forming a breathing gas block with the breathing gas spaces and breathing gas connections;

connecting a valve plate to the block;

positioning a heating foil as a heating element adjacent to one or more of the breathing gas spaces; and placing a cover over the block, the block and the cover cooperating to enclose the spaces as breathing gas conduits with the heating foil disposed adjacent to one or more of the conduits;

determining condensate portions of the breathing spaces where condensate occurs;

determining non-condensate portions of the breathing spaces which are free from condensate;

applying the heating foil to the condensate portions;

causing the non-condensate portions to be free of the heating foil.

20. A method in accordance with claim 19, further comprising:

determining relative amounts of condensate occurring at the condensate portions;

varying an amount of heating created by the heating foil according to the relative amounts of condensate occurring.

21. A breathing gas flow control system, comprising:

a breathing gas block with breathing gas connections;

a cover, said block and said cover cooperating to enclose breathing channels;

a valve arranged at a location between said breathing gas block and said cover; and a heating device for heating one or more of breathing gas channels, the heating device including a heating foil provided as a heating element adjacent to one or more of the breathing gas channels;

said breathing gas channels have condensate portions where condensate occurs;

said breathing gas channels have non-condensate portions which are free from condensate;

said heating foil is arranged on said condensate portions;

said non-condensate portions are free of the heating foil.

22. A system in accordance with claim 21, wherein:

different amounts of condensate occurs at said condensate portions;

said heating foil provides different amounts of heating according to said different amounts of condensate occurring.

* * * * *